United States Patent
Pusch et al.

(10) Patent No.: US 10,952,875 B2
(45) Date of Patent: *Mar. 23, 2021

(54) METHOD FOR CONTROLLING AN ORTHOPEDIC JOINT

(71) Applicant: OTTO BOCK HEALTHCARE GMBH, Duderstadt (DE)

(72) Inventors: Martin Pusch, Duderstadt (DE); Herman Boiten, Ede (NL); Sven Zarling, Jecksberg (DE)

(73) Assignee: Ottobock SE & Co. KGAA, Duderstadt (DE)

(*) Notice: Subject to any disclaimer, the term of this patent is extended or adjusted under 35 U.S.C. 154(b) by 198 days.

This patent is subject to a terminal disclaimer.

(21) Appl. No.: 15/881,537

(22) Filed: Jan. 26, 2018

(65) Prior Publication Data

US 2018/0177617 A1 Jun. 28, 2018

Related U.S. Application Data

(63) Continuation of application No. 12/741,303, filed as application No. PCT/DE2008/001821 on Nov. 5, 2008, now Pat. No. 9,877,849.

(30) Foreign Application Priority Data

Nov. 7, 2007 (DE) .......................... 102007053389.8

(51) Int. Cl.
*A61F 2/64* (2006.01)
*A61F 2/70* (2006.01)
(Continued)

(52) U.S. Cl.
CPC ................ *A61F 2/60* (2013.01); *A61B 5/112* (2013.01); *A61B 5/4851* (2013.01); *A61F 2/68* (2013.01);
(Continued)

(58) Field of Classification Search
None
See application file for complete search history.

(56) References Cited

U.S. PATENT DOCUMENTS

| 5,383,939 A | 1/1995 | James |
| 5,662,693 A | 9/1997 | Johnson et al. |
| (Continued) | | |

FOREIGN PATENT DOCUMENTS

| CA | 2651124 A1 | 11/2007 |
| DE | 19859931 A1 | 7/2000 |
| (Continued) | | |

OTHER PUBLICATIONS

Dietl, H., et al., "Der Einsatz von Electronik Bei Prothesen zur Versorgung der unteren Extremitaet," Med. Orth. Tech., 117 (1997), pp. 31-35.

*Primary Examiner* — David H Willse
(74) *Attorney, Agent, or Firm* — Holland & Hart LLP

(57) ABSTRACT

A method for controlling an orthopedic joint of a lower extremity in at least one degree of freedom by an adjustable actuator for adjusting an orthopedic apparatus to walking situations that differ from walking on a plane. The orthopedic apparatus comprises top connecting members to connect to a limb, and an orthopedic element that is hingedly arranged distal to the connecting members. The method includes sensing, with sensors, several parameters of the orthopedic apparatus; comparing the sensed parameters with criteria that have been established based on several parameters and/or parameter curves and are stored in a computer unit; selecting a criterion that is suitable on the basis of the determined parameters and/or parameter curves; and adjusting resistances to movements, extents of movements, driving forces, and/or the progresses thereof in accordance with (Continued)

the selected criterion in order to control special functions that differ from walking on a plane.

21 Claims, 6 Drawing Sheets

(51) Int. Cl.
    *A61F 2/60*    (2006.01)
    *A61B 5/11*    (2006.01)
    *A61B 5/00*    (2006.01)
    *A61F 2/68*    (2006.01)
    *A61F 2/76*    (2006.01)
    *A61F 5/01*    (2006.01)
    *A61F 2/66*    (2006.01)
    *A61F 2/50*    (2006.01)
    *A61F 2/74*    (2006.01)

(52) U.S. Cl.
    CPC .................. *A61F 2/70* (2013.01); *A61F 2/64* (2013.01); *A61F 2/6607* (2013.01); *A61F 2002/5006* (2013.01); *A61F 2002/5033* (2013.01); *A61F 2002/5035* (2013.01); *A61F 2002/6818* (2013.01); *A61F 2002/701* (2013.01); *A61F 2002/704* (2013.01); *A61F 2002/741* (2013.01); *A61F 2002/745* (2013.01); *A61F 2002/763* (2013.01); *A61F 2002/764* (2013.01); *A61F 2002/7625* (2013.01); *A61F 2002/7635* (2013.01); *A61F 2002/7645* (2013.01); *A61F 2005/0155* (2013.01)

(56) References Cited

U.S. PATENT DOCUMENTS

| | | | |
|---|---|---|---|
| 6,610,101 | B2 | 8/2003 | Herr et al. |
| 6,755,870 | B1 | 6/2004 | Biedermann et al. |
| 7,637,959 | B2 | 12/2009 | Clausen et al. |
| 9,877,849 | B2 * | 1/2018 | Pusch ............... A61F 2/68 |
| 2002/0052663 | A1 | 5/2002 | Herr et al. |
| 2003/0120183 | A1 | 6/2003 | Simmons |
| 2006/0184280 | A1 | 8/2006 | Oddsson et al. |
| 2006/0224246 | A1 | 10/2006 | Clausen et al. |
| 2006/0249315 | A1 | 11/2006 | Herr et al. |
| 2007/0050047 | A1 | 3/2007 | Ragnarsdottlr et al. |
| 2007/0056592 | A1 | 3/2007 | Angold et al. |
| 2007/0233279 | A1 * | 10/2007 | Kazerooni ............ A61F 2/68 623/24 |
| 2009/0171468 | A1 | 7/2009 | Pusch et al. |
| 2010/0185124 | A1 * | 7/2010 | Bisbee, III ........... A61F 2/64 600/595 |

FOREIGN PATENT DOCUMENTS

| | | | |
|---|---|---|---|
| DE | 102006021802 | A1 | 11/2007 |
| EP | 0549855 | A2 | 7/1993 |
| EP | 1058524 | B1 | 9/2004 |
| GB | 2367753 | A | 4/2002 |
| JP | 59071746 | A | 4/1984 |
| JP | 05-212070 | | 8/1993 |
| JP | 2001218778 | A | 8/2001 |
| JP | 2001514925 | A | 9/2001 |
| JP | 2002533161 | A | 10/2002 |
| JP | 2003527926 | A | 9/2003 |
| JP | 2007524483 | A | 8/2007 |
| RU | 2089138 | C1 | 9/1997 |
| RU | 2271779 | C2 | 3/2006 |
| WO | 9908621 | | 2/1999 |
| WO | 0172245 | A2 | 10/2001 |
| WO | 0172245 | A3 | 3/2002 |
| WO | 2005079712 | A2 | 9/2005 |
| WO | 2005087144 | A2 | 9/2005 |
| WO | 2006024876 | A2 | 3/2006 |
| WO | 2006069264 | A1 | 6/2006 |
| WO | WO 2007/016781 | A1 * | 2/2007 ............ H02K 7/18 |

* cited by examiner

METHOD FOR CONTROLLING AN ORTHOPEDIC JOINT

TECHNICAL FIELD

The invention relates to a method for controlling an orthopedic joint of a lower extremity in the flexion and/or extension direction by means of an adjustable actuator for adapting an orthopedic appliance to walking situations that deviate from walking on the plane. The orthopedic appliance comprises upper means of attachment to a limb, and an orthopedic element arranged in an articulated manner distally of the attachment means.

BACKGROUND

DE 10 2006 021 802, as a later published document, relates to the control of a passive prosthetic knee joint with adjustable damping in the direction of flexion such that a prosthetic appliance, with upper attachment means and with a connection element to an artificial foot, which is secured on the prosthetic knee joint, can be adapted for climbing stairs. The low-torque lift of the prosthetic foot is detected, and the flexion damping in the lift phase is then reduced to below a level that is suitable for walking on a plane.

SUMMARY

Proceeding from this prior art, the object of the invention is to make available a method for controlling an orthopedic joint, with which method it is possible to take account of particular walking situations and to ensure a suitable behavior of the orthopedic appliance.

According to the invention, this object is achieved by a method having the features of the main claim. Advantageous embodiments and developments of the method are set forth in the dependent claims.

In the method according to the invention for controlling an orthopedic joint, which is understood to include prosthetic joints and also orthotic joints of a lower extremity, in at least one degree of freedom, an adjustable actuator is used to permit adaptation to different walking situations, for example by changing the damping in the flexion and/or extension direction.

The orthopedic appliance in which the orthopedic joint is integrated can be an orthosis or prosthesis, for example a prosthetic knee joint with distal attachment means for a prosthetic foot and with proximal attachment means to a limb. Provision is also made for the orthopedic appliance to comprise only a prosthetic foot joint with an artificial foot secured thereon and with attachment means to a below-knee stump. In addition to the exoprostheses, knee or ankle joint orthoses are also provided that can be controlled using the method. In the case of orthopedic knee joints, the orthopedic element arranged in an articulated manner distally of the attachment means is formed, in orthoses, by the below-knee rails with the foot holder, and, in prostheses, by the below-knee shaft with the prosthetic foot. In the case of orthopedic appliances for the ankle joint, a foot holder and means for securing on the lower leg are to be provided for orthoses, and a prosthetic foot with means of attachment to a lower leg are to be provided in prostheses.

Sensors are arranged on the orthopedic appliance and detect several parameters of the orthopedic appliance or of the limb. These detected parameters are compared with criteria that have been established on the basis of several parameters and/or parameter profiles. On the basis of these criteria, which are stored in a computer unit and which assign specific movement states or load states of the orthopedic appliance to specific walking situations, a specific criterion is selected that is regarded as the most suitable on the basis of the detected parameters and/or parameter profiles. It is possible in principle that several criteria also have to be regarded as suitable on the basis of the determined parameters or parameter profiles. Then, either a selection is made on the basis of additional criteria, or several special functions are superposed. The sensors determine the parameters during walking, preferably during walking on a plane, such that the user of the orthopedic appliance has the possibility of initiating the special functions without having to perform movements that are not consistent with the natural pattern. By virtue of slight deviations of individual parameters being detected during walking and being evaluated in correlation with other parameters and deviations, which have been combined to form criteria, it is possible for forthcoming movement sequences to be estimated, such that the special function can be initiated from walking. While it is known from the prior art to activate special functions through unusual movement sequences when standing, e.g. through repeated and rapid loading of the front foot or through an undulating movement resulting from atypical alternate loading of the heel and front foot, it is possible, with the method according to the invention, to effect a change-over from walking, which results in an "intuitive" control that does not require any deliberate maneuvers. This increases the wearing comfort and improves safety, particularly for prosthesis wearers, since incorrect operation is minimized or excluded.

In order to control special functions that deviate from walking on a plane, provision is made that movement resistances, movement ranges, drive forces and/or the profiles thereof are adapted in accordance with the selected criterion. The special function is controlled or initiated on the basis of the selected criterion or of the selected criteria, and this comprises, for example, the flexion damping and/or extension damping being adapted to a level that deviates from the level suitable for walking on a plane, a catch being released, a drive being adjusted and/or a limit stop being adjusted. By changing the setting of the passive components such as hydraulics, brakes or limit stops, no additional kinetic energy is supplied to the orthopedic appliance, such that it is also possible in this context to talk of passive actuators. Adjustment of the passive actuators, e.g. reduction of a cross section of flow by moving a slide, also requires energy, but this does not result in an increase of the kinetic energy of the prosthesis or orthosis. Active actuators are understood as pumps, electric drives or the like, which can actively assist the movement sequence. The actuators used can be switches, pumps, electric motors, energy stores or other drives. The energy stores are provided in the form of, for example, springs, pressure accumulators or the like, from which the energy stored therein can be released in a controlled manner to an appliance.

In this way, it is possible to perform special functions, e.g. alternating climbing of stairs, with a prosthetic knee joint, and to make climbing stairs easier for a prosthesis wearer, without the danger of the prosthetic leg suddenly buckling or being left suspended below a step. It is thus also possible to be able to call up the special functions from different starting positions, for example when walking up stairs is to be performed from standing, with the prosthetic side first or with the contralateral side first, when the first step is to be taken or when the last step is reached. It is likewise possible to call up the special function from a starting position via several different criteria, if several criteria significantly indicate a specific, expected walking pattern or an expected walking situation. This as a whole permits an automatic control of the joint, without the user of the orthopedic appliance deliberately having to perform a maneuver that deviates from a natural movement sequence.

It is thus possible for the prosthesis/orthosis wearer to be provided with an orthopedic appliance that adapts to the particular situation, without the need for a long period of accustomization to the extended function. The invention exploits the fact that the relevant starting positions and walking situations have a specific, significant loading or loading sequence or parameter sequence, which are suitable for establishing criteria for calling up special functions and for correspondingly changing the degrees of freedom, in particular the damping, such as the flexion damping and/or extension damping.

In particular, a control of a passive joint is possible with the adjustment of the damping, and provision is likewise made that a catch, for example a limit stop catch, is released or set, or a limit stop is adjusted, such that a variable flexion angle can be realized. In addition, it is possible for a drive to be adjusted, such that specific elements of the orthopedic appliance are actively adjusted, for example a support of the extension movement or of a flexion movement in the foot or in the knee joint.

As a parameter of the criteria that are used to trigger one or more special functions, it is possible to use the axial force or the profile of the axial force in the components of the orthopedic appliance, for example in the below-knee rail of an orthosis or in the below-knee shaft of a knee prosthesis. The force profile used in this case is an increase or a decrease in an axial force, the change in the profile of an axial force, and the speed of a decrease in an axial force. In order to determine these parameters, force sensors are used which determine the axial force within the orthopedic appliance. By repeated measurement, preferably in short cycles, the profile of the axial force can then be determined.

Provision is also made that the parameter used and taken into account in the selection of special functions is the joint angle or the profile of a change in the joint angle. The change in the joint angle is determined in the form of a pivoting speed or of an acceleration about the joint axis during walking. The joint angle can be used, for example, to determine the relative position of the components of the orthopedic appliance, and this makes it possible to detect specific phases of walking and to draw conclusions from this regarding the walking situation that is to be expected and/or to determine or estimate the load that is to be expected on the orthopedic appliance.

Moreover, the torque acting in the joint, a change in the joint torque or a profile of a change in the joint torque can be used as parameters, since every walking situation can at a specific point in time be assigned a specific torque value. From the joint torque in one phase itself, or from the profile of the change in the joint torque, it is possible to determine whether and in which walking situation the user of the orthopedic appliance is located and which additional damping adjustments have to be performed in order to support the next walking situation in the best possible manner.

Provision is further made that a vertical movement of at least one component of the orthopedic appliance is detected and is used as a parameter for determining the initiation of a special function, when this parameter, together with other parameters, lies within a specific value range and thus satisfies fixed criteria. In addition to a purely vertical movement, which is likewise detected via corresponding sensors, a profile of a vertical movement can also be used as parameter, that is to say the speed of a vertical movement or a vertical acceleration, in order to determine in which starting position the patient is located and which walking situation is to be expected.

Surprisingly, it has been found that a horizontal movement and/or a profile of a horizontal movement can also be used as parameter. When climbing stairs using an orthopedic appliance, it has been shown that, during walking, a lower leg that is guided rearward, i.e. counter to the direction of walking, supplies reliable signals. The knee is in this case positioned clearly in front of the ankle joint in the direction of walking.

It is likewise useful, for control of the orthopedic appliance, if a tilt angle of part of the orthopedic appliance in space is determined, that is to say the inclination that a component has in space. This can either be measured via an absolute angle sensor, which has a spatial orientation as reference variable, for example the direction of gravitational force, or can be computed from various other sensor data. In addition to the instantaneous tilt angle, it is likewise possible for a change in the tilt angle and the profile of the change in the tilt angle of part of the orthopedic appliance to be used as a parameter in order to decide which special functions are initiated, and when they are initiated, in the damping of the orthopedic appliance. The tilt angle can be determined from the acceleration and angular velocity that were recorded by acceleration sensors and a gyroscope.

Preferably, several parameters or parameter profiles are combined in one criterion, that is to say two or more parameters, in order to determine the starting state as accurately as possible on the basis of the sensor data and to reach a precise association and decision as to which special function is initiated.

Provision is likewise made that several criteria or the meeting of several criteria can initiate a special function. This takes account of the fact that a special function, for example the alternating climbing of stairs, is started from different walking speeds, different positions, or with the prosthetic leg first or the healthy leg first. It can therefore happen that precisely one special function has to be initiated, but different criteria can be satisfied in order to ensure that precisely this special function is initiated.

In a development of the invention, the control method, in the special function, increases the extension damping and/or flexion damping in a set-down and hip-straightening phase of the lower extremity to a level above a damping of a swing phase control for walking on a plane. In this way, it is possible to effect a controlled extension or straightening both of the hip joint and also of the knee joint and ankle joint.

To climb over an obstacle, it is necessary that, in the lift phase, the flexion damping is first reduced and then the extension damping, so as to ensure that the greatest possible step can be taken, since an obstacle has to be overcome, for example the threshold of a door or an object lying on the ground, and the foot or prosthetic foot is not intended to be set down on a next higher step. After the foot has been set down, however, provision is made that, in the special function, the flexion damping and/or extension damping in the set-down phase is increased to a maximum value, this applies both to alternating climbing of stairs and also to overcoming obstacles, such that the knee joint, when straightening, is secured against buckling or against hard contact with the end stop. Provision is likewise made that, directly before the foot or prosthetic foot is set down, the extension damping is increased before the straightening, such that the positioning of the foot or prosthetic foot can be effected by the hip angle that is directly controllable by the patient. Increasing the flexion damping to a maximum value has the advantage that, if the hip-straightening moment is inadequate, giving-way of the knee is reduced or avoided. The high degree of damping in the set-down and hip-straightening phase is in this case preferably maintained until straightening of the hip is complete.

The original flexion damping within the joint can preferably be increased in accordance with the change in the knee angle, since a great deal of information concerning the starting state can be determined from the knee angle. As soon as a fixed knee angle is reached that is generally greater than a knee angle suitable in swing phase control for walking on a plane, the flexion damping is increased. Alternatively or in addition, the flexion damping can be increased or decreased in accordance with the axial force acting on the below-knee shaft or on the below-knee component. If the axial force drops sufficiently quickly to approximately 0 with the knee almost straight, this is an indicator for initiation of a stair-climbing mode, such that a specific control can be effected within the damper devices.

Provision is alternatively made that, in the case of an orthopedic knee joint, the special function is initiated when an axial force acting on the below-knee shaft drops to a specific value and when the knee joint is straightened or being straightened, and the flexion damping is reduced in the special function. The absolute value of the axial force can be used as an additional parameter in order to define a criterion. If the axial force drops below a fixed level, the special function is initiated, and the flexion damping is then reduced in the special function.

In addition or alternatively, provision is made that, in the case of an orthopedic knee joint, the special function is initiated when the lower leg is inclined rearward, the knee joint is straightened and a knee torque is below a fixed level, and, in the special function, the flexion damping is reduced to below a fixed value. A rearwardly inclined lower leg is present when the knee joint is located clearly in front of the ankle joint.

Provision is likewise made for the special function to be initiated when there is an upward vertical acceleration and when an axial force is below a fixed level, which special function effects a change in the flexion damping and/or extension damping, and for the flexion damping to be reduced in the special function.

In one variant, the special function is initiated when there is a rearward horizontal acceleration, that is to say counter to the direction of walking, and when an axial force is below a fixed level, and the flexion damping is reduced in the special function.

The flexion damping and/or extension damping is adjusted preferably during the lift phase and/or set-down phase, for example when the foot or the prosthetic foot is set down again after being lifted and an increase in the axial force is then determined. Likewise, with a knee angle remaining approximately constant, the extension damping and flexion damping can be increased, since this is associated with a low mechanical resistance and can therefore be performed with relatively little energy. The flexion damping can be reduced in the lift phase to a minimum value, such that the damping effective in every system on account of friction is not further increased.

Alternatively, provision is made that the damping is adjusted during the stance phase or swing phase.

It is likewise possible that a low-torque lift of the distally arranged orthopedic element is detected via a force sensor or torque sensor, said detection being able to take place mechanically, likewise the change in the various dampings, in order to obtain the simplest possible structure of the orthopedic appliance that is to be controlled. After the low-torque lift of the distal orthopedic element has been detected, the flexion damping can likewise be reduced, specifically to a level that is below a level suitable or optimized for walking on a plane.

By means of the reduction in the flexion resistance, by reducing the flexion damping, it is possible to obtain a joint angle that allows a prosthetic foot or a foot to be set down on a next step up. With a hip flexion and a low-torque lift of a prosthetic foot or of the distally arranged orthopedic element, a knee angle can be obtained which, in the event of the hip being brought forward or in the event of a corresponding extension by the force of gravity, is sufficient to overcome the edge of a step or to climb over an obstacle and position the prosthetic foot or the distally arranged orthopedic element over the step or set it down behind the obstacle. It is advantageous for the weight to be distributed in such a way that the center of gravity is arranged as far distally as possible, such that, without an increase in the overall weight of the orthopedic appliance, the desired effect of the knee flexion is reached with a low-torque lift of the prosthetic foot or of the distally arranged orthopedic element.

A low-torque lift can be detected by measurement of a horizontal acceleration of the distally arranged orthopedic element and by detection of a bending in the joint.

In principle, provision is likewise made for flexion to be supported in the lift phase via a pretensioned spring mechanism; in addition to a flexion of the knee, a plantar flexion of the foot can also take place, such that the front part of the foot is set down.

After the flexion damping has been reduced, a free extension can be set with time control, such that only the system-inherent resistances are active in the extension direction. The time control can be effected mechanically or electrically. The parameters are preferably determined during walking, in order to be able to permit a change via the actuators without interrupting the movement sequence.

In addition to control in the extension direction or flexion direction, provision is likewise made for control in another degree of freedom, e.g. in the medial-lateral direction, or in combined forms thereof.

Such control is expedient, for example, in hip joints or ankle joints. Other rotary or translatory degrees of freedom can also be influenced by the control.

BRIEF DESCRIPTION OF THE DRAWINGS

Illustrative embodiments of the invention are explained in more detail below with reference to the figures, in which.

DETAILED DESCRIPTION

Figure 1:
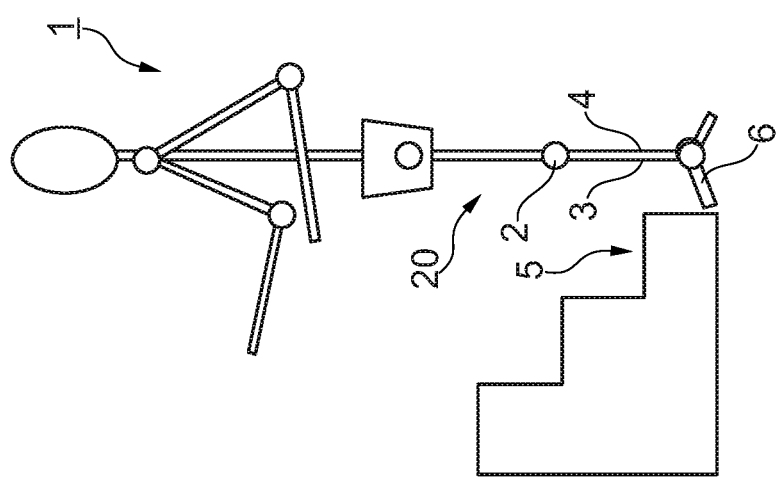

FIG. 1 shows a prosthesis wearer 1 with a knee joint prosthesis 2, which is secured by upper attachment means to a thigh stump. The prosthetic leg 20 stands with the healthy contralateral leg 4 in front of a step.

Figure 2:
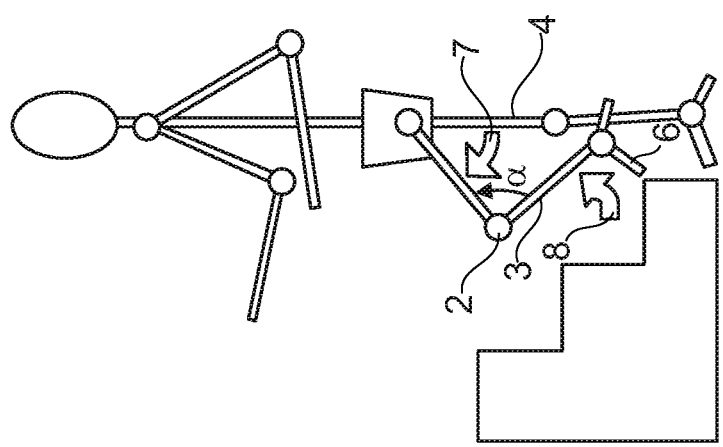

To reach the next step up, a prosthetic foot 6 has to be guided over the step edge. An active bending of the hip, as is indicated by the arrow 7, assists the passive bending of the knee, which is shown by the arrow 8 and which, because of the mass inertia both of the prosthetic foot 6 and also of the connection element 3, is effected from the prosthetic knee joint 2 to the prosthetic foot 6. For this purpose, a minimum flexion damping is required to ensure that, after a flexion of the hip, the prosthetic foot 6 does not swing forward and is not moved against the riser or under the step 5. In the lift phase, as shown in FIG. 2, the aim is for the prosthetic foot 6 to be guided upward, as far as possible in a perpendicular manner, this possibly being initiated by a slight rearward movement. The lift is detected via the flexion angle between the connection element 3 and the thigh or via a reduction of the axial force in the connection element 3, without flexion of the prosthetic foot 6. It is also possible to detect the stair-climbing mode, and thus the lowering of the flexion damping to a value below the normal swing phase control, preferably to the minimum value, via a horizontal rearward movement of the prosthetic foot 6 in conjunction with a bending of the hip.

Figure 3:
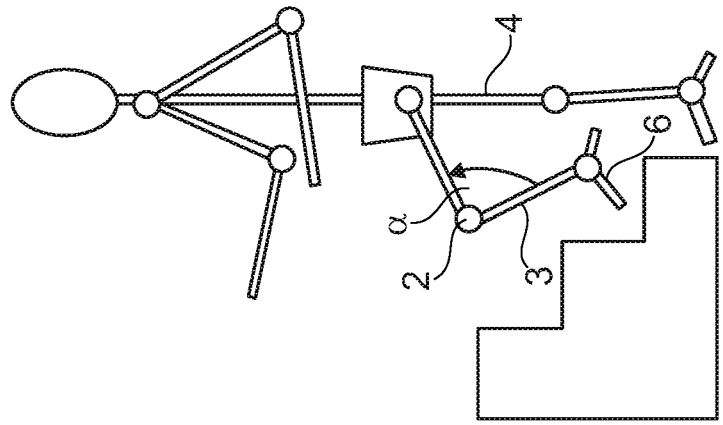
FIGS. 1 to 6 show a schematic sequence of alternating stair-climbing with a passive knee joint prosthesis.

After the step edge has been negotiated and the lift phase completed, as is shown in FIG. 2, a secure positioning of the prosthetic foot 6 on the step is required. For this purpose, the prosthetic foot 6 has to be moved forward, which can be achieved by extension as a result of the force of gravity. For this purpose, an extension damping can be reduced, if this has not already been done in the lift phase. A prosthetic knee joint 2 that is sufficiently damped in flexion and extension prior to straightening allows the prosthesis wearer 1 to position the prosthetic foot 6, by means of the hip angle being changed. In the lowering and hip-straightening phase, the flexion and extension are preferably strongly damped in order not only to control the set-down, but also to prevent spontaneous falling back in the event of the hip-straightening torque being insufficient. The extension remains damped so as to be able to control the speed of straightening of the hip and knee. This is shown in FIG. 3.

Figure 4:
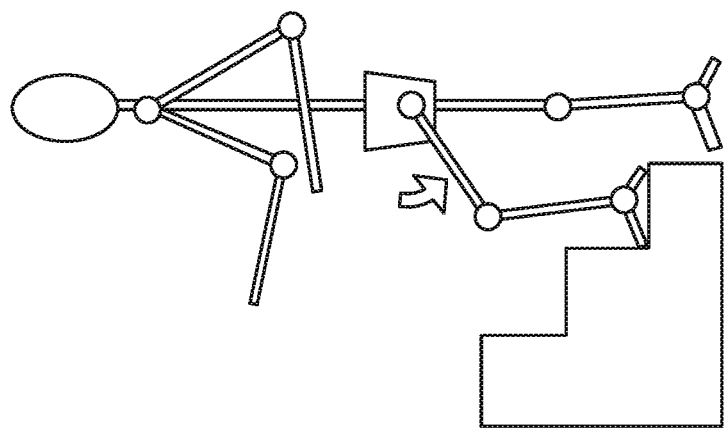

In FIG. 4, the set-down phase is completed. The prosthesis wearer 1 can initiate straightening of the knee with a hip-straightening torque. The straightening of the knee can be assisted by an extension of the healthy foot.

Figure 5:
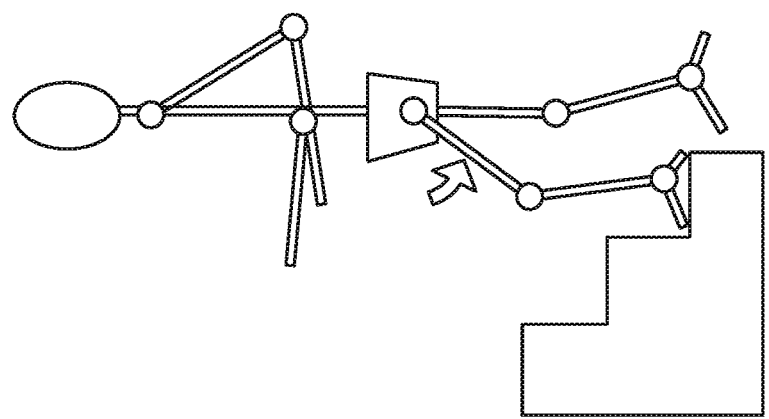

FIG. 5 shows the increasing straightening of the knee through application of a hip torque. The increasing straightening of the knee shortens the effective lever and facilitates the straightening of the knee through the straightening of the hip.

Figure 6:
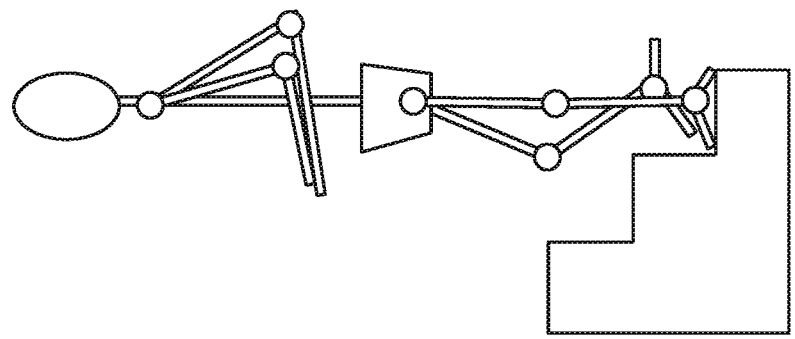

FIG. 6 shows the complete extension of the leg provided with the knee joint prosthesis 2. The contralateral leg 4 is moved past the prosthetic leg 20 and placed on the next step up, such that alternating climbing of stairs is possible with the passive knee joint prosthesis.

Accordingly, the control is configured in such a way that, during the lift of the prosthetic foot 6, a flexion resistance is set that permits a knee angle $\alpha$, which allows the prosthetic foot 6 to be placed on the next step. Flexion support by spring mechanisms may facilitate the lifting movement and make it easier to negotiate the step height.

If no action is to take place after the stair-climbing mode has been triggered by detection of a low-torque lift, a free extension is set, said free extension being set in a time-dependent manner. The time function can also be mechanical. The low-torque lift can be detected via the mass inertia, if the healthy leg is first set down and only the second step is intended to be negotiated by the leg provided with the prosthesis. If the prosthetic foot is first unloaded and the prosthetic knee joint then bent, the stair-climbing mode is to be set. The damping both in the direction of extension and also in the direction of flexion after the lift phase, that is to say during the hip-straightening phase, is maintained until a complete extension of the prosthetic knee joint is reached or detected.

Figure 7:
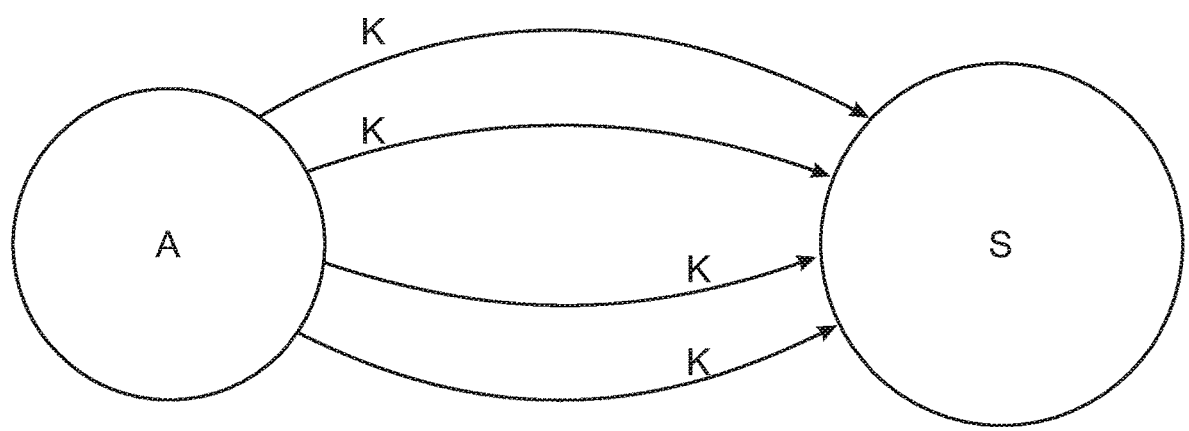
FIG. 7 shows a schematic depiction of the method.

FIG. 7 shows a schematic depiction of the method. Proceeding from a starting position A, which is detected by sensors on the prosthesis or orthosis, the sensor data are compared with predefined values or value ranges that have been stored in a memory unit and have been combined to form various criteria K. Several signal states or signal profiles from the sensors preferably describe a criterion K.

If, for example, a specific axial force in connection with a knee angle or with a vertical movement is measured, corresponding values of the sensors can result in the criterion that the special function S of overcoming an obstacle is to be set, which leads to a corresponding adjustment of the extension damping and flexion damping. Similarly, the criterion K for the special function S of overcoming an obstacle can be satisfied when there is a rapid drop in the axial force, when the knee is straightened or being straightened and when the axial force is below a level, such that corresponding damper adjustments have to be made. The detected criteria K trigger the respectively required actions, for example a reduction or increase in the flexion damping and/or extension damping, the release of a catch, the adjustment of a drive, or the adjustment or canceling of a limit stop.

The overcoming of obstacles can also be detected, for example, when an axial force drops below a defined level and a knee is straightened, likewise a criterion can be reached by satisfying a defined inclination of the lower leg or of a below-knee rail in space, a knee angle and a low knee torque. A vertical acceleration upward, with a straightened knee and with a relatively low axial force level, can likewise be a criterion for a special function, for example the overcoming of an obstacle or alternating climbing of stairs.

It is further possible, proceeding from the starting position A, to compare several signal states or profiles with various criteria K. The comparing of several criteria K with one another, and of several signal states in one criterion K, provides increased safety. The greater the number of signal states or profiles within a criterion K, the more precisely it is possible to determine the respective state of the orthopedic appliance or of the patient, and the walking situation is thereby also more precisely described. On the basis of this information and of the signal states or profiles within the parameters provided for a criterion K, it is then possible, for example, to specifically change the damper characteristics and the movement pattern of the orthopedic appliance.

Several criteria K can trigger the same special function K, thereby providing greater safety in respect of correct detection of a movement state. This is necessary in view of the fact that special functions S, such as stepping over an obstacle or alternating climbing or descending of stairs, differ significantly in terms of their movement patterns from those of walking on a plane, but this special function S is difficult to detect from walking on a plane. Whereas this was previously made easier by particularly pronounced movements being performed in order to set a special function S, for example a repeated rocking movement of the front of the foot, the method according to the invention permits automatic adaptation of the damping behavior to the particular walking situation.

Walking on a plane normally requires shortening of the leg that is to be moved forward after the foot is lifted. If the leg is not shortened, sufficient ground clearance can be generated by lifting of the hip or circumduction. Physiologically, the leg is also shortened by bending of the knee. In leg prostheses that replace the knee and the lower leg, the weight relationships of the lower leg, and the time and motor factors involved in walking, have the effect that the lower leg swings too far rearward and, consequently, the leg prosthesis is not straightened in time and cannot therefore be loaded. Patients therefore walk very slowly, or the prostheses are equipped with a suitable swing phase control that significantly damps the swing behavior of the lower leg. High-performance flexion damper systems take account of different walking speeds and always provide enough freedom of the leg to ensure that the prosthesis users do not stumble, but the leg is straightened again in time for the following loading phase. The more quickly the user walks, the more the damping takes effect.

To climb stairs, a knee has to be bent much more than when walking on a plane, so as to avoid the leg being left suspended in front of the edge of the step that is to be negotiated. The reduced flexion damping can also be exploited in order to overcome small obstacles in one step. However, for the reasons mentioned above, the low flexion damping necessary for this purpose is not suitable for walking on a plane. For detection of the respectively required flexion damping for the step that is to be taken, a plurality of sensor data can be combined within one criterion and can trigger a special function when corresponding parameters are satisfied. If the tilting of the lower leg in space is evaluated, a low flexion resistance for climbing stairs can be activated when the prosthesis or orthosis is unloaded and the knee is not bent. If the prosthesis leg is unloaded with the knee straightened, a low flexion resistance for climbing stairs can be activated by the speed of the reduction in load even before the prosthesis is completely unloaded. The user in this way has more time to initiate bending. In order to ensure that flexion damping is not deactivated too early, for example when a drop in axial force is detected while standing in a vehicle traveling over bumpy ground, the absolute value of the axial force can be used as additional parameter for a criterion.

It is likewise possible, by evaluating the angle profiles of the thigh and lower leg, to distinguish between climbing stairs and walking on a plane. If the thigh is bent slightly rearward, a reduction of the flexion damping can be expected.

For control of an ankle joint, it is advantageous to determine when the toe area or the front of the foot is move rearward in order to overcome a step or an obstacle. No dorsal flexion should be allowed when the heel is set down, so as to make climbing stairs easier.

Accordingly, the resistance to a dorsal flexion is increased after set-down. By contrast, when going down a set of stairs, a strong plantar flexion is desirable at set-down. In order to permit complete set-down of the prosthetic foot or of the foot holder, a dorsal flexion should be permitted, but this should be done increasingly with a resistance in order to ensure controlled set-down.

In principle, a resistance to straightening is also necessary in the joint appliance, particularly in the knee joint, in order to teach a patient active control and action. Orthopedic knee joints that permit walking down a set of stairs are known from the prior art. By means of a high degree of damping in the flexion direction, the user of the orthopedic appliance can bend the knee joint in a controlled manner and thus reach the next step. The high degree of flexion damping results in a uniform movement and thus relieves the load on the contralateral side. When climbing stairs, the movement in a healthy knee joint is supported by a knee-straightening torque. This torque is provided by muscles. Orthopedic appliances are known that comprise a knee joint which permits straightening of the knee by means of actuators. Because of the energy required and the forces that occur, a relatively heavy knee joint is needed that is dependent on external energy.

In the case of orthoses or prostheses of the lower extremity, it is in many cases possible to generate a sufficiently high straightening torque from the hip in order to straighten the knee when climbing stairs. However, as soon as the knee begins to straighten, it moves rearward, relative to the center of gravity of the body, such that the knee-straightening torque increases. This effect is self-intensifying. The increasing effective lever arm results in uncontrolled straightening, with a hard, uncomfortable end stop. In order to adapt the orthopedic appliance to climbing stairs without external energy being supplied, provision is made for the control to significantly increase the extension damping via an adjustable actuator after set-down on the next step up. This damping acts counter to the straightening torques acting on the knee joint and is preferably chosen so as to permit an almost constant and easily controllable straightening. This can be ensured simply by constant damping. It is likewise possible to provide damping that increases with straightening, in order to compensate for the effect whereby, with increasing straightening of the knee joint relative to the center of gravity of the body, the knee joint is exposed to a greater effective lever arm.

The set-down on the next step up, with a bent knee joint, can optionally be performed via sensors arranged on the orthopedic appliance or via an actuator that can be activated mechanically upon set-down, for example a piston that is displaceable in the joint as a result of the axial force on the orthopedic appliance. The extension damping is in this case increased to a level that markedly exceeds the level for walking on a plane.

Figure 8:
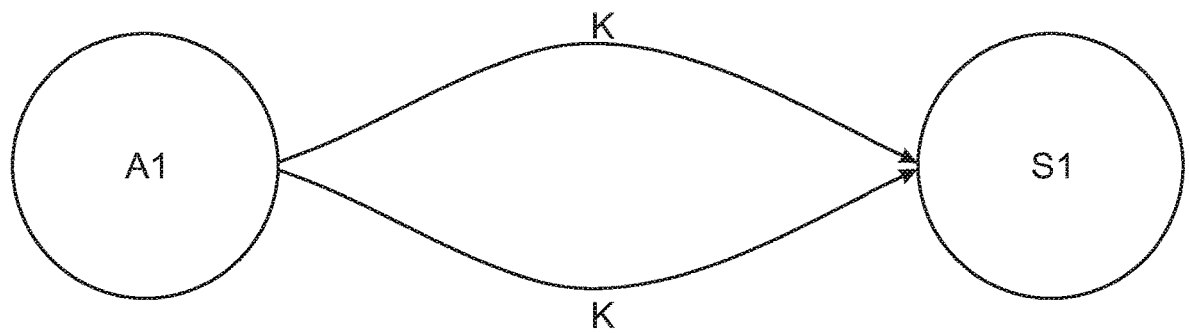
FIGS. 8 to 10 show variants of the method.

FIG. 8 shows a variant of the invention in which, proceeding from a starting position A1, a special function S1 can be called up via several criteria K. If several parameters are determined on the orthopedic appliance, different parameters can be combined to foam different criteria. It is thus possible for two different criteria to lead to the initiation of a special function S.

Figure 9:
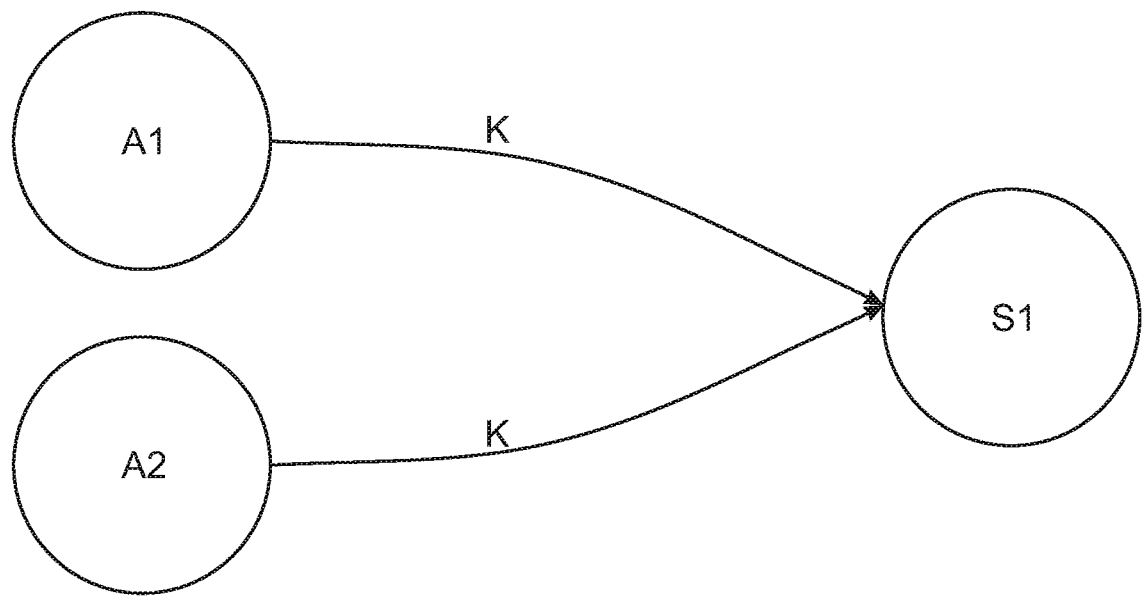

FIG. 9 shows a variant of the invention in which, proceeding from different starting positions A1, A2, exactly one special function S1 can be called up via different criteria K.

Figure 10:
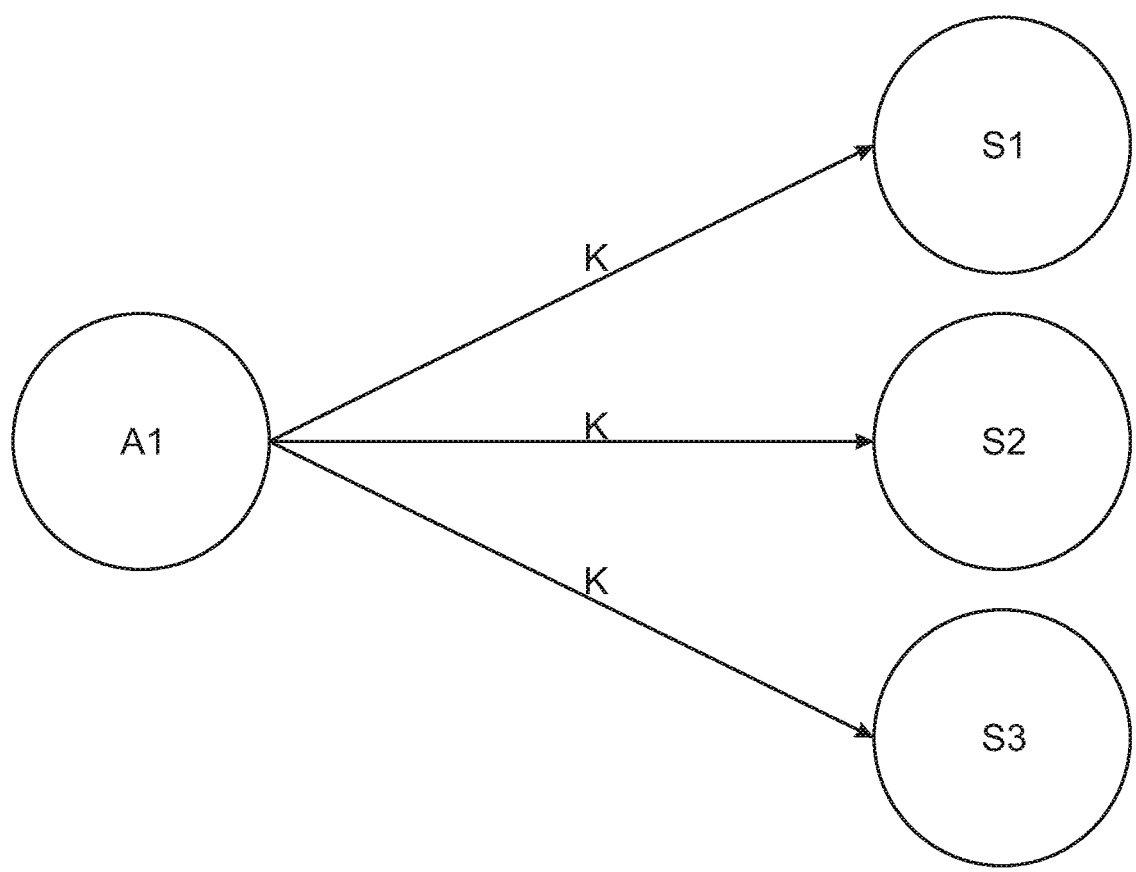

FIG. 10 finally shows that it is possible, from one starting position A1, to switch to various special functions S1, S2, S3 via various criteria K and parameter profiles. It can thus happen that identical instantaneous values of the respective parameters are present in the starting situation A1, for example axial force, knee angle and torque, but different walking situations can be predicted from the profiles of these parameters and, as a result, corresponding special functions S1, S2, S3 can be initiated, by means of drives being switched on or off, energy stores being released, damper devices varied or brakes activated. Similarly, limit stops can be adjusted and catches released.

We claim:

1. A method for controlling a passive prosthetic knee joint, the method comprising:
   providing a prosthesis having the passive prosthetic knee joint, an upper attachment member configured to attach to a limb, a lower attachment member pivotally attached to the upper attachment member, an actuator, a computer unit, and a plurality of sensors;
   detecting parameters of the prosthesis with the plurality of sensors, the parameters including at least an absolute angle of the lower attachment member relative to a vertical axis, a rate of change of the absolute angle, a torque force in the knee joint, and a rate of change of the torque force;

comparing the detected parameters with criteria stored in the computer unit;

selecting multiple criteria based on the comparing;

automatically adjusting, with the actuator, at least one of a damping force or a damping profile for the knee joint in accordance with the selected criteria, to adapt to special functions that deviate from walking on a planar surface.

2. The method as claimed in claim 1, wherein the parameters further include at least one of a joint angle and a profile of a change in the joint angle.

3. The method as claimed in claim 2, wherein at least one of the special functions is initiated when a lower leg is inclined rearward, the passive prosthetic knee joint is straightened, and a knee torque is below a fixed level.

4. The method as claimed in claim 1, wherein the parameters further include at least one of an axial force and a profile of the axial force.

5. The method as claimed in claim 1, wherein the parameters further include at least one a vertical movement and a profile of a vertical movement.

6. The method as claimed in claim 1, wherein the parameters further include at least one of a horizontal movement and a profile of a horizontal movement.

7. The method as claimed in claim 1, wherein the parameters further include at least one of a tilt angle of part of the prosthesis in space and a profile of a change in the tilt angle of part.

8. The method as claimed in claim 1, wherein at least two parameters or parameter profiles are combined in one criteria.

9. The method as claimed in claim 1, wherein multiple criteria are used to initiate one or more of the special functions.

10. The method as claimed in claim 1, wherein in at least one of the special functions, the damping is automatically changed in a set-down phase or a hip straightening phase.

11. The method as claimed in claim 1, wherein at least one of the special functions is initiated when an axial force acting on a lower leg drops and when the passive prosthetic knee joint is straightened or being straightened.

12. The method as claimed in claim 11, wherein the at least one of the special functions additionally takes into account an axial force dropping below a fixed level.

13. The method as claimed in claim 1, wherein the parameters further include at least one of a vertical acceleration and an axial force, and the special function is initiated when there is an upward vertical acceleration and when an axial force is below a fixed level.

14. The method as claimed in claim 1, wherein the parameters further include at least one of a horizontal acceleration and an axial force, and the special function is initiated when there is a rearward horizontal acceleration and when an axial force is below a fixed level.

15. The method as claimed in claim 1, wherein the damping is adjusted during at least one of a lift phase and the set-down phase.

16. The method as claimed in claim 1, wherein the damping is adjusted during a stance phase or during a swing phase.

17. The method as claimed in claim 1, wherein a low-torque lift of the distally arranged lower attachment member is detected via a force sensor or torque sensor.

18. The method as claimed in claim 1, wherein the parameters further include at least one of a vertical acceleration of the distally arranged lower attachment member and a joint angle, and a low-torque lift is detected by measurement of the vertical acceleration and by detection of a bending in the passive prosthetic knee joint.

19. The method as claimed in claim 1, wherein after the automatic adjustment of the damping force or damping profile, setting a free extension with time control.

20. The method as claimed in claim 19, wherein the time control is effected mechanically or electronically.

21. The method as claimed in claim 1, wherein the parameters are determined during walking.

* * * * *